United States Patent [19]
Watanabe et al.

[11] Patent Number: 5,389,555
[45] Date of Patent: Feb. 14, 1995

[54] PARTICLE PATTERN JUDGING METHOD

[75] Inventors: Haruhisa Watanabe, Hachioji; Satoshi Tanaka, Hino; Shinya Matsuyama, Hachioji; Keita Sembu, Tokorozawa, all of Japan

[73] Assignee: Olympus Optical Co., Ltd., Tokyo, Japan

[21] Appl. No.: 80,592

[22] Filed: Jun. 24, 1993

Related U.S. Application Data

[63] Continuation of Ser. No. 629,705, Dec. 18, 1990, abandoned.

[30] Foreign Application Priority Data

Dec. 21, 1989 [JP] Japan ................................. 1-329662
Jul. 13, 1990 [JP] Japan ................................. 2-184333

[51] Int. Cl.6 ........................ G01N 21/75; G01N 33/80
[52] U.S. Cl. .............................. 436/164; 436/63; 436/805; 422/73; 356/39; 356/434; 356/441; 73/64.41; 382/6
[58] Field of Search .................... 436/34, 63, 69, 164, 436/518, 805; 422/73; 356/39, 434, 441; 382/6; 364/413.01; 73/64.41; 358/107

[56] References Cited

U.S. PATENT DOCUMENTS

| | | | |
|---|---|---|---|
| 4,556,641 | 12/1985 | Kano | 436/165 |
| 4,563,430 | 1/1986 | Kano | 436/164 |
| 4,575,492 | 3/1986 | David et al. | 436/164 |
| 4,727,033 | 2/1988 | Hijikata | 436/69 |
| 4,794,450 | 12/1988 | Saito | 358/93 |

FOREIGN PATENT DOCUMENTS

| | | |
|---|---|---|
| 165551 | 12/1985 | European Pat. Off. . |
| 0198327 | 10/1986 | European Pat. Off. . |
| 257660 | 3/1988 | European Pat. Off. . |
| 3422616 | 12/1985 | Germany . |
| 61-215948 | 9/1986 | Japan . |
| 62-105031 | 5/1987 | Japan . |

*Primary Examiner*—David A. Redding
*Attorney, Agent, or Firm*—Stevens, Davis, Miller & Mosher

[57] ABSTRACT

Particle pattern judging method in which a particle pattern formed on the bottom surface of a reaction vessel by an immunological agglutinated reaction is measured in an optical manner; a variation ratio of light intensity of the border of the particle pattern is obtained and the particle pattern is judged whether it is agglutinated or not on the basis of the variation ratio: or a two-dimensional image of the particle pattern is picked up; the two-dimensional image of the particle pattern is differentiated to obtain differentiated values concerning pixel compositions consisting of the particle pattern; and the particle pattern is judged whether it is agglutinated or not on the basis of a distribution of the thus obtained differentiated values. By the method according to the invention, it is possible to judge whether the particle pattern is agglutinated or not in an exact manner, even when bubbles are included in the particle pattern, or the particle pattern is destroyed, or the particle pattern is torn or the agglutinating force of the particle pattern is weak.

6 Claims, 6 Drawing Sheets

FIG_1A

FIG_1B

FIG_2A

FIG_2B

FIG_3

FIG_4

FIG_5

FIG_6

FIG_7A

FIG_7B

FIG_12

PARTICLE PATTERN JUDGING METHOD

This application is a continuation of application Ser. No. 07/629,705, filed Dec. 18, 1990, now abandoned.

BACKGROUND OF THE INVENTION

1. Field of the Invention

The present invention relates to a particle pattern judging method, in which a specimen and a reagent are mixed in a reaction vessel to cause an immunological agglutinating reaction therein, and a particle pattern formed on the bottom surface of the reaction vessel is measured in an optical manner to be automatically judged whether the particle pattern is agglutinated or not and the other property of the pattern on a clinic purpose.

2. Prior Art Statement

In Japanese Patent Laid-open Publication No. 58-105065, there is disclosed a conventional particle pattern judging method in which the particle pattern formed on the bottom surface of the reaction vessel by the agglutinating reaction is measured in an optical manner and a ratio in brightness between a central portion of the reaction vessel and a peripheral portion thereof is obtained to judge whether the particle pattern is agglutinated or not on the basis of the ratio. Such technique for judging particle patterns is also disclosed in U.S. Pat. No. 4,727,033, in which light intensities of central and peripheral portions of the inclined bottom surface of the reaction vessel are separately measured by using two light receiving elements and the judgement whether the particle pattern formed on the bottom surface is agglutinated or not is conducted on the basis of a ratio between the output of the light receiving element for measuring the light intensity of the central portion of the bottom surface and the output of the light receiving element for measuring the light intensity of the peripheral portion thereof. That is to say, when the particle pattern is agglutinated, the particles are uniformly deposited on the bottom surface of the reaction vessel so that the difference between the light intensities of the light receiving elements is small; in contrast thereto, when the particle pattern is not agglutinated, the particles are fallen down the inclined bottom surface of the reaction vessel and collected in the central portion thereof so that the difference between the light intensities of these two light receiving elements becomes large. In such conventional particle pattern judging method, the thus obtained ratio is compared with predetermined upper and lower limits; and when the ratio is larger than the upper limit, the particle pattern is judged as an agglutinated pattern, when the ratio is smaller than the lower limit, the particle pattern is judged as a non-agglutinated pattern, and when the ratio is between the upper and lower limits, the particle pattern is judged as ambiguous and thus it is impossible to judge the ambiguous pattern.

Further, in Japanese Patent Laid-open Publication Nos. 61-215948, 62-105031, 63-58237 and 63-256839, there is disclosed another particle pattern judging method in which agglutinating reactions are conducted in a number of wells formed in a microplate and an optical image of the wells is picked up by a television camera; the image data of each well is processed by a computer to obtain an area where the particles are deposited on the bottom surface of each well and the particle pattern is judged whether it is agglutinated or not on the basis of the thus obtained area.

According to the method disclosed in Japanese Patent Preliminarily Laid-open Publication No. 63-58237, an image of bottom surface of each well formed in the microplate is picked up by a television camera to obtain image signals thereof; data of a center point of the well is obtained by processing the thus obtained image signals; then a contour of particle pattern formed in the well is obtained by obtaining the difference in brightness between the image signal inside of a circle, which is formed around the center point, and the image signal outside of the circle; then the area inside the thus obtained contour is obtained; this area is then compared with a predetermined standard value. When the area is larger than the standard value, the particle pattern is judged as an agglutinated pattern and when the area is smaller than the standard value, the particle pattern is judged as a non-agglutinated pattern. That is to say, in this conventional method, the particle pattern is judged by the number of pixels corresponding to the particles collected in the center portion of the well.

Further, in Japanese Patent Preliminarily Laid-open Publication No. 63-256839, there is disclosed another judging method, in which the center point of the well is obtained in the same way mentioned above; and the judgement is conducted by utilizing a relative relation between a dimension of the center portion, where the particle are deposited, on the bottom surface of the reaction vessel and a standard deviation of a differential coefficient of the particle pattern.

However, in the above mentioned conventional methods, there is a drawback that it is not possible to judge whether the particle pattern is agglutinated or not in an exact manner. In case the agglutination force of the particles to be tested is so weak that there is a great possibility that an agglutinated pattern having almost the same shape as that of a non-agglutinated pattern is formed on the bottom surface of the reaction vessel: it is very difficult to automatically judge such particle patterns exactly. Therefore, in the conventional method, the reliability of judgement is so low that an operator has to check the patterns in a visual manner and correct the result judged by an automatic particle pattern judgement apparatus. Additionally much labor is therefore necessary. In the method disclosed in JP 58-105065 and U.S. Pat. No. 4,272,033, there is a problem that the number of specimens which are judged as ambiguous becomes large, because, the agglutinating reaction is generally very delicate so that there are many cases where the ambiguous particle patterns are formed. Therefore, efficiency in processing the specimens decreases and human mistakes occur frequently. Thus, an analysing accuracy and a reliability of the judgement are decreased.

In the method disclosed in Japanese Patent Preliminarily Laid-open Publication No. 63-58237, it is possible to determine the central point of the particle pattern exactly, but a dimension of the portion where the particles are deposited on the bottom surface of the vessel not only depends upon whether the particles are agglutinated or not but also depends upon the amount of the specimen or the reagent. Therefore, it is very difficult to conduct an exact judgement.

Furthermore, in the method disclosed in Japanese Patent Preliminarily Laid-open Publication No. 63-256839, the judgement result is apt to be influenced by bubbles included in the test liquid as well as the fact that the pattern gets out of its shape or the pattern is torn; thus it is also impossible to judge the pattern exactly.

SUMMARY OF THE INVENTION

The present invention has for its purpose to withdraw the drawback mentioned in the above and provide a particle pattern judging method, in which it is possible to judge whether the particle pattern is agglutinated or not in an exact manner even when the agglutinating force of the particles to be tested is weak; it is possible to conduct exact judgement without being influenced by the bubbles included in the test liquid or the fact that the pattern gets out of shape or that the pattern is torn. In the method according to the invention, the number of specimens, which need to be re-examined by the operator in a visual manner, is decreased and thus judgement can be conducted efficiently with a high reliability.

In order to carry out the purpose, the particle pattern judging method according to the invention comprises the following steps:

measuring a particle pattern formed on a bottom surface of a reaction vessel by an immunological agglutinating reaction in an optical manner to obtain a first measurement data of the particle pattern;

extracting a second measurement data concerning a border of the particle pattern from the first measurement data of the particle pattern to obtain a variation ratio of the second measurement data of the border; and judging whether the particle pattern formed in the reaction vessel is agglutinated or not on the basis of the thus obtained variation ratio of the second measurement data of the border of the particle pattern.

Figure 1A:
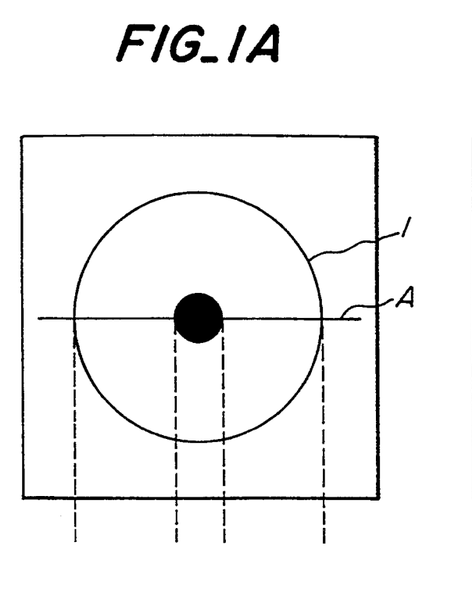
FIGS. 1A and 1B are schematic views showing particle patterns formed in reaction vessels.
Figure 1B:
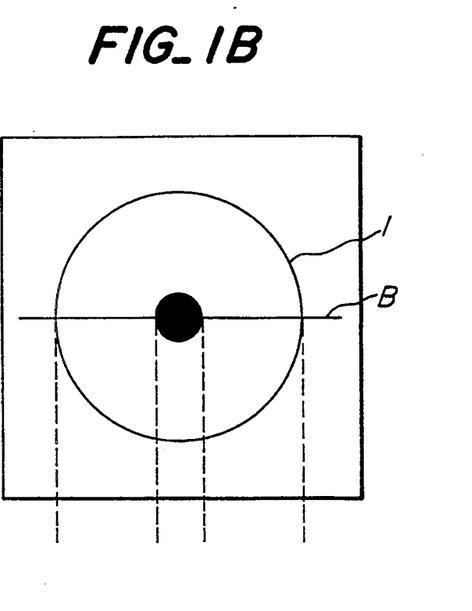

When a test liquid including particles to be tested is delivered in a reaction vessel having a conical bottom surface, there are sometimes shown non-agglutinated particle patterns having almost the same shape of an agglutinated particle pattern, because the agglutinating force of the test liquid is very weak. FIG. 1A shows an example of such non-agglutinated particle patterns and FIG. 1B shows the agglutinated particle patterns. However, there is found a property that the border of the agglutinated pattern shown in FIG. 1B is ambiguous in comparison to the border of the non-agglutinated pattern shown in FIG. 1A. In the method according to the present invention, it is possible to distinguish such non-agglutinated particle pattern having the almost same shape as that of the agglutinated pattern from the agglutinated particle pattern by utilizing the property.

Figure 2A:
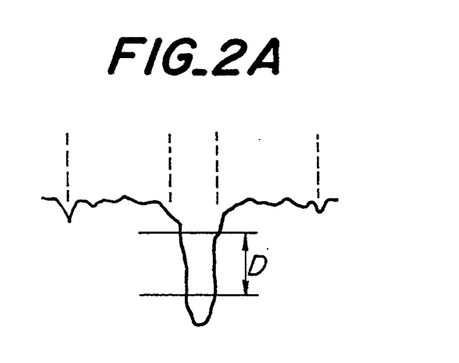
FIGS. 2A and 2B are schematic views depicting light amounts transmitted on straight lines A and B which pass at centers of the reaction vessels shown in FIGS. 1A and 1B; these figures are to explain the function of the present invention.
Figure 2B:
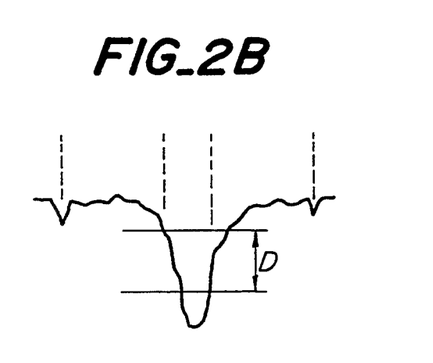

FIGS. 2A and 2B show a variation of a light amount transmitted through the reaction vessel and the test liquid contained therein on straight lines A and B which pass center points of the reaction vessels 1 illustrated in FIGS. 1A and 1B. When paying its attention to borders, which are shown by ↕ D, of the particle patterns, it can be found that the variation ratio of the light amount transmitted on the border of the agglutinated particle pattern in FIG. 2B is smaller than that of the non-agglutinated particle pattern shown in FIG. 2A. Therefore, by extracting measurement data of the light amount on the borders from the measurement data on the light amount on the straight lines A and B as a whole and checking the variation ratio of the measurement data on the border, it is possible to distinguish the agglutinated particle pattern, in which the agglutinating force is weak, from the non-agglutinated particle pattern.

It should be noted that it is possible to obtain the variation ratio of the light amount on the border by extracting image data on the border of the straight line which passes the center of the particle pattern from image data of the bottom surface of the reaction vessel as a whole, or extracting image data on one part of or the whole of the border from the image data of the bottom surface, and then processing the extracted image data in the computer. Further to this, the border of the particle pattern can also be detected such that an intermediate brightness is counted on the basis of brightness of the center portion of the bottom surface of the vessel and the peripheral portion thereof and a portion having such intermediate brightness is detected as the border. In this case, by checking the variation ratio of the measurement data concerning the portion having the intermediate brightness, it is possible to distinguish the agglutinated particle pattern formed by the weak agglutinating force from the non-agglutinated particle pattern exactly.

The method according to the present invention has the other aspect which comprises the steps of:

picking up a two dimensional image of a particle pattern formed on the bottom surface of a reaction vessel by an immunological agglutinating reaction to obtain an image information of the particle pattern;

differentiating said image information to obtain differentiated value of said image information:

judging whether the particle pattern is agglutinated or not on the basis of a distribution of the differentiated value of the image information.

In the judging method according to the aspect of the invention, even when bubbles are contained in the particle pattern, or the pattern gets out of shape and the pattern is torn, the particle pattern can be judged exactly. That is to say, since in the case the bubbles are contained in the pattern, an image density of the contour portion of the bubbles becomes high; and in case an image density of the destroyed portion or the torn portion of the pattern becomes high and the image density of the lower portion of the destroyed portion or the torn portion becomes low; therefore it is possible to judge such an unusual pattern from the distribution of the differentiated values of the two-dimensional image signal of the pattern. Therefore, according to the method of the invention, it is possible to judge the particle pattern exactly without being influenced by the bubbles, the destruction or the tearing of the pattern. Additionally, the number of specimens, which need to be re-examined in a visual manner, becomes small, thus the analysing efficiency is increased. Furthermore, in comparison to the conventional particle pattern judging method, judging error caused by the variation of the delivering amount of the specimen or the reagent is apt to be decreased, because in the method of the invention, it is the judgement whether the pattern is agglutinated or not depends only upon information of the area of the portion where the particles are deposited.

DETAILED EXPLANATION OF THE PREFERRED EMBODIMENTS

Figure 3:
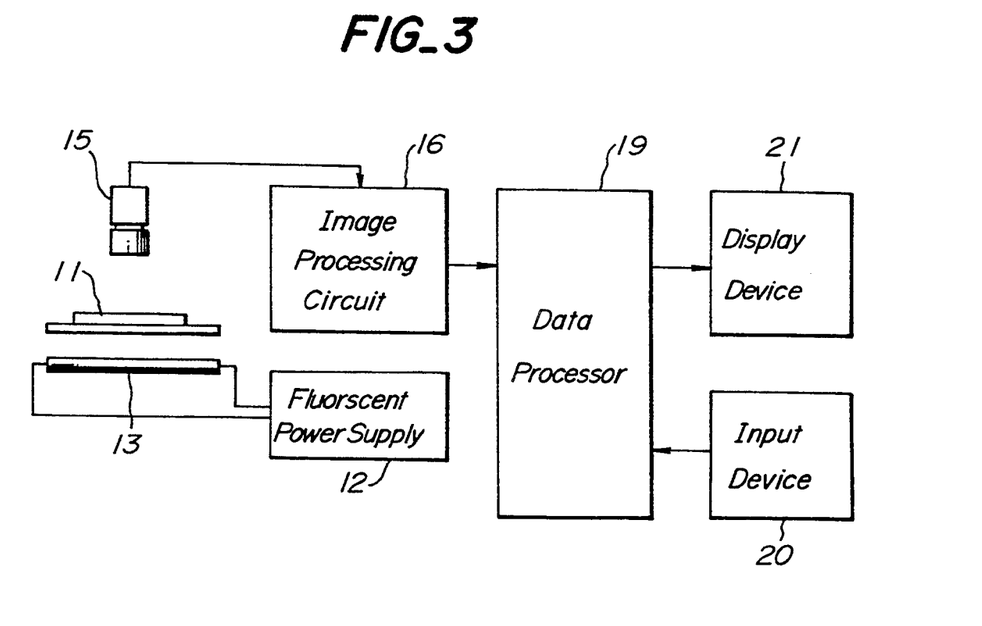
FIG. 3 is a block diagram illustrating one example of a structure of an automatic particle pattern judging apparatus in which a first embodiment of the method according to the invention is executed.
Figure 4:
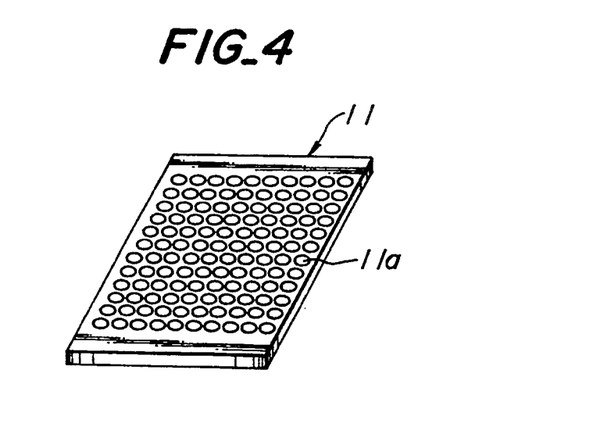
FIG. 4 is a schematic view representing a structure of a microplate which is used in the apparatus illustrated in FIG. 3.

FIG. 3 is a block diagram showing the structure of an automatic particle pattern judging apparatus in which a first embodiment of the present invention is carried out. In this embodiment, a microplate 11, in which a number of wells 11a are formed in a matrix manner as shown in FIG. 4, are used as reaction vessels. It should be noted that the microplate 11 is made of a transparent material such as acrylic resin. As shown in FIG. 3, the microplate 11 is illuminated by a fluorescent lamp 13 from the bottom surface side of the microplate 11. The fluorescent lamp 13 is connected to a fluorescent power supply 12. Each well 11a of the microplate 11 has a conical bottom surface; a test liquid including particles to be tested is contained in the well 11a; and a particle pattern is formed on the bottom surface of the well 11a by standing the microplate in a static manner after a specimen and agent are mixed in the well 11a.

An image of the bottom surface of each well 11a, which is illuminated by the fluorescent lamp 13, is picked up by a video camera 15, which is arranged above the microplate 11 in a successive manner and the thus obtained image data is supplied to an image processing circuit 16. In the image processing circuit 16, a mean amount of a variation ratio of a light intensity on a border of the particle pattern, i.e. an intermediate portion between the central portion and the peripheral portion is obtained on the basis of the image data of the well 11a. It should be noted that the image data of the bottom surface of the well 11a is successively picked up by the video camera 15 by relatively moving the microplate 11 and the video camera 15 in two-dimensional manner.

Figure 5:
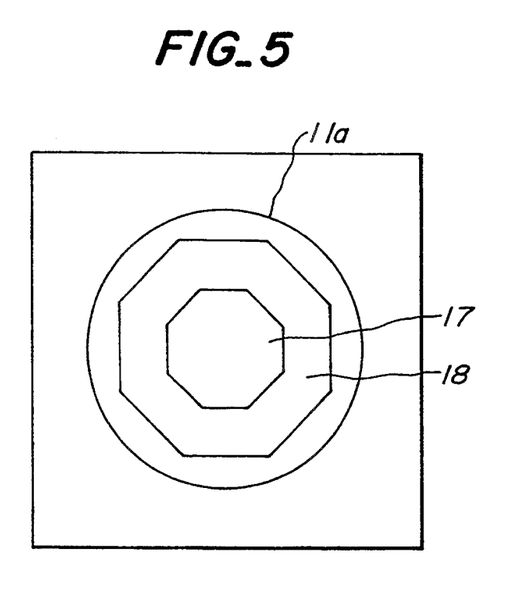
FIG. 5 is a schematic view showing one of wells formed in the microplate, in which areas for obtaining a mean value of the variation ratio of the light amount are preliminarily indicated.

Data processing conducted in the image processing circuit 16 will be explained in the following:

In the image processing circuit 16, the image data of the bottom surface of the well 11a is firstly converted to digital data. This conversion is carried out such that a bright image data is converted to a large digital data and a dark image data to a small digital data. Next, a given amount of the digital data corresponding to a predetermined central portion 17 of the bottom surface of the well 11a and a given amount of the digital data corresponding to a peripheral portion 18 are picked up, respectively. FIG. 5 shows the predetermined central and peripheral portions of the bottom surface of the well 11a. Then, a mean value C of the digital data of the central portion 17 and a mean value P of the digital data of the peripheral portion 18 are obtained. Thereafter, a predetermined positive value is added to the mean value C to obtain a value c; and a predetermined positive value is subtracted from the mean value P to obtain a value p. Further, data x satisfying a condition of $p > x > c$ is extracted from the digital data of the center portion 17 of the well 11a to obtain data of the border of the particle pattern. It should be noted that such data of the border of the particle pattern are shown by references D in FIGS. 2A and 2D. Further, the extracted data is differentiated in a two-dimensional manner or in a one-dimensional manner to obtain a variation ratio of the light amount transmitted on the border and a mean value X thereof.

The thus obtained mean value X of the variation ratio of the light amount transmitted on the border is supplied to a data processor 19. In the data processor 19, the mean value X is compared with a given standard value to judge whether the pattern formed in the well 11a is agglutinated or not; and the judgement result is displayed on a display device 21 in accordance with instructions from an input device 20 such as a keyboard.

In such a manner, image data on the border of the particle pattern are extracted from the image data of the bottom surface of the well 11a to obtain the variation ratio of the image data; and the particle pattern is judged in accordance with the variation ratio. Therefore, in case the particle pattern is agglutinated by a weak agglutinating force, it is possible to automatically judge the pattern as an agglutinated one, in an exact manner, and to get a judgement result with high reliability. By the method according to the invention, since the operator's check and correction of the judgement result in a visual manner is unnecessary, the labor of the operator is decreased, considerably.

In the first embodiment, in order to pick up the image data of the bottom surface of each well 11a, it is arranged such that the microplate 11 and the video camera 15 are relatively moved in two-dimensional manner. It may be possible to arrange such that an image data of the microplate 11 as a whole firstly picked up and then an image data of each well 11a is extracted from the whole image data of the microplate 11 to process the image data of the pattern in the same manner.

Figure 6:
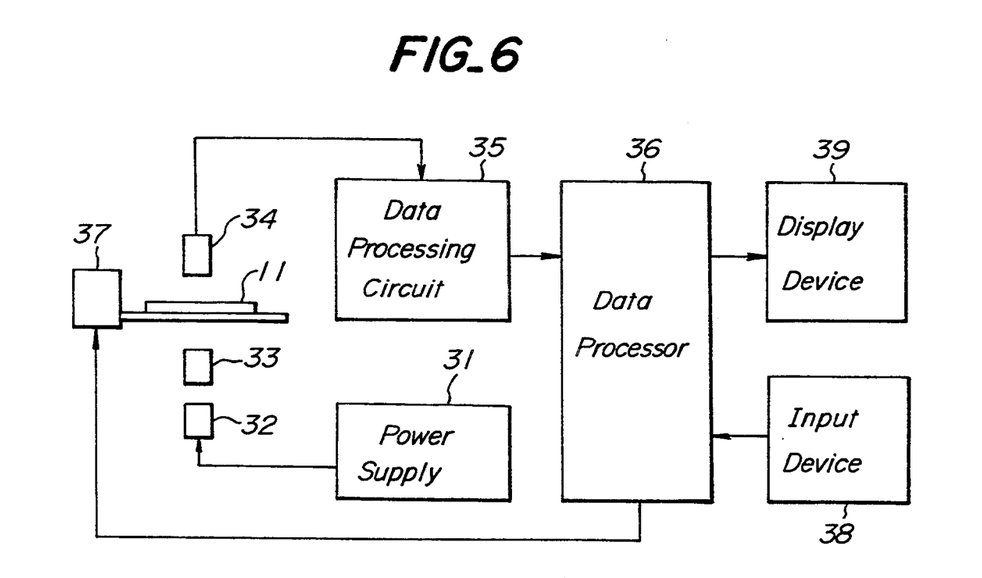
FIG. 6 is a block diagram depicting another example of the structure of the automatic particle pattern judging apparatus in which a second embodiment of the method according to the invention is executed.
Figure 7A:
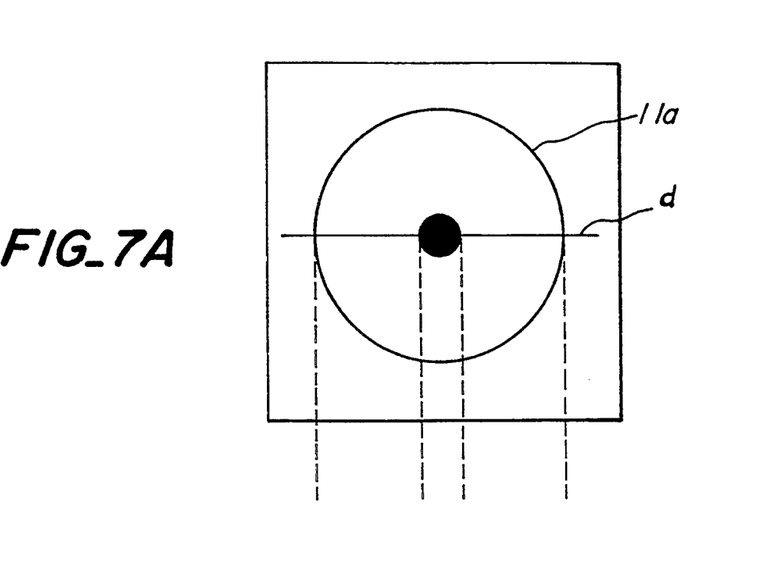
FIGS. 7A and 7B are schematic view illustrating the particle pattern formed in a well of the microplate and a variation of the light amount transmitted on a straight line C: these figures are for explaining the function of the second embodiment shown in FIG. 6.
Figure 7B:
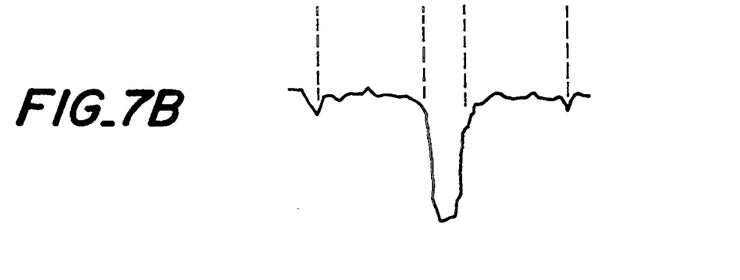

FIG. 6 is a block diagram showing another structure of the automatic particle pattern judging in which the second embodiment of the method according to the invention is conducted. In this embodiment, the microplate 11 is illuminated from the bottom surface side by a spot by means of a light source 32 via a lens group 33, and the light spot transmitted through the microplate 11 and the test liquid contained therein is received by a light receiving device 34. An output of the light receiving device 34 is converted to a digital signal in a data processing circuit 35; and the digital signal is supplied to a data processor 36. The microplate 11 is arranged to be movable in a horizontal plane by means of a microplate transferring mechanism 37 under the control of the data processor 36. By this movement of the microplate 11, the well 11a is scanned in a direction of the diameter d as shown in FIG. 7A; and a transmitted light amount data on the diameter d is shown in FIG. 7B. It should be noted that the analogue-digital conversion in the data processing circuit 35 is conducted such that the bright data is converted to a large digital data and the dark data to a small digital data.

In the second embodiment, the transmitted light amount data shown in FIG. 7B is obtained in such a manner; and a mean value of the variation ratio of the light amount transmitted on the border of the particle pattern between the central portion and the peripheral portion is obtained in the data processor 36 in accordance with the transmitted light amount data.

The data processing conducted in the data processor 36 will be explained as follows:

In the data processor 36, the mean value C of the predetermined central portion on the diameter d concerning each well 11a of the microplate 11 is firstly obtained as well as the mean value P of the predetermined peripheral portion on the diameter D of the well 11a. Next, the mean value C is multiplied by a given positive value, which is larger than one (1), to obtain a value c; and the mean value P is multiplied by a given value, which is smaller than one (1), to obtain a value p; wherein the given values c and p should satisfy the condition of p>c. Next, a data satisfying the condition of p>x>c is extracted from the data on the diameter D concerning the relevant well 11a to extract a data on the border between the central portion and the peripheral portion of the diameter D. Further, by differentiating the extracted data to obtain a variation ratio of the transmitted light amount on the border and then a mean value X of the variation ratio is obtained.

Thereafter, the mean value X is compared with a given standard value to judge that the pattern formed in the relevant well 11a is agglutinated or not.

After the particle pattern is judged in the data processor 36 in such manner, the judgement result is displayed on a display device 39 in accordance to instructions from an input device 38 such as a keyboard.

As stated in the above, since the variation ratio of the light amount transmitted on the border of the particle pattern on the diameter D is obtained from the data representing a light amount distribution transmitted on the diameter D of the well 11a, and whether the particle pattern is agglutinated or not is judged from the variation ratio of the transmitted light amount, it is possible to automatically judge the particle pattern in an exact manner even in the case that the agglutinating force of the particles to be tested is small, and a high reliability can be obtained as well as the first embodiment.

Figure 8:
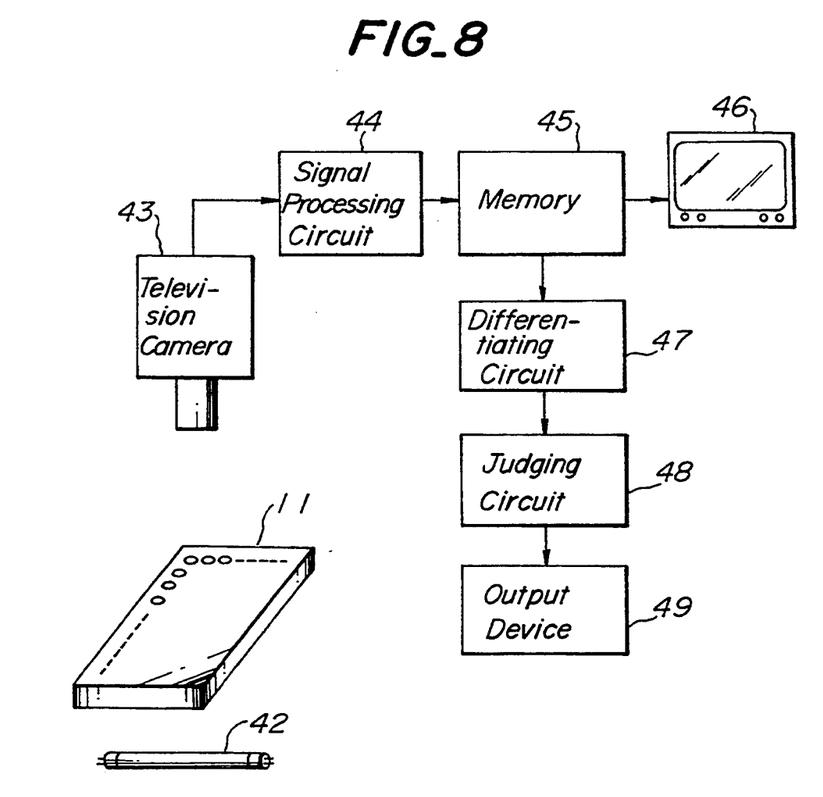
FIG. 8 is a block diagram representing other example of the structure of the automatic particle pattern judging apparatus in which a third embodiment of the method according to the invention is executed.
Figure 9:
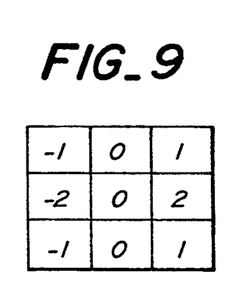
FIGS. 9 and 10 are schematic views showing differentiating operators for detecting variations of the light intensities in horizontal and vertical directions of the particle pattern.
Figure 10:
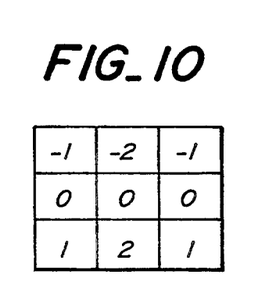
Figure 11:
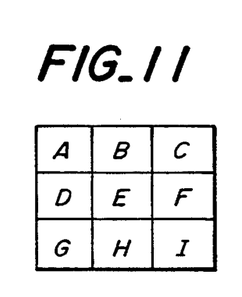
FIG. 11 is a schematic view depicting a pixel composition for differentiating the image signals.

FIG. 8 is a schematic view showing a whole structure of the automatic particle pattern judging apparatus in which a third embodiment of the particle pattern judging method according to the present invention is carried out. In the third embodiment, the microplate 11 is put on a driving table (not shown) and the driving table is arranged to be movable with respect to an optical axis of an image pick up device 43. Under the microplate 11, a light source 42 is arranged; and above the microplate 11, the image pick up device 43 is arranged to pick up a two-dimensional image of the particle pattern formed in the bottom surface of each well 11a of the microplate 11. In the third embodiment, a CCD television camera is used as the image pick up device 43. A two-dimensional image information of the particle pattern produced in the image pick up device 43 is supplied to a signal processing circuit 44 to be amplified and converted to a digital signal; and the digital signal is supplied to a memory device 45 to be stored therein. The image information stored in the memory device 45 is read out and supplied to a monitor 46 to display the particle pattern formed on the bottom surface of the well 11a of the microplate 11 on a monitor screen of the monitor 46. In the third embodiment, the two-dimensional image information read out by the memory device 45 is supplied to a differentiating circuit 47 to obtain a differentiated value of the image information. The differentiating operation is conducted by using differentiating operators as explained in the following FIGS. 9 and 10 show the differentiating operators; a first operator shown in FIG. 9 is for detecting a variation of the light intensity of the image in a horizontal direction and a second operator shown in FIG. 10 is for detecting a variation of the light intensity of the image in a vertical direction. As shown in FIG. 11, nine pixels, which are adjusted to each other, consisting of pixel area is extracted from the image information of the particle pattern in a successive manner. The light intensity value of each pixel consisting of this pixel area is multiplied by each corresponding coefficient of the first and second differentiating operators; and the thus obtained multiplied values of the light intensity are added to each other to obtain the sums Y1 and Y2 in accordance with the following formulae. Further, a mean value of these sums Y1 and Y2 is obtained to obtain a differentiated value Y of the pixel area.

$$Y1 = (-1 \times A) + (0 \times B) + (1 \times C)$$
$$+ (-2 \times D) + (0 \times E) + (2 \times F)$$
$$+ (-1 \times G) + (0 \times H) + (1 \times I)$$

$$Y2 = (-1 \times A) + (-2 \times B) + (-1 \times C)$$
$$+ (0 \times D) + (0 \times E) + (0 \times F)$$
$$+ (1 \times G) + (2 \times H) + (1 \times I)$$

$$Y = (|Y1| + |Y2|)/2$$

Figure 12:
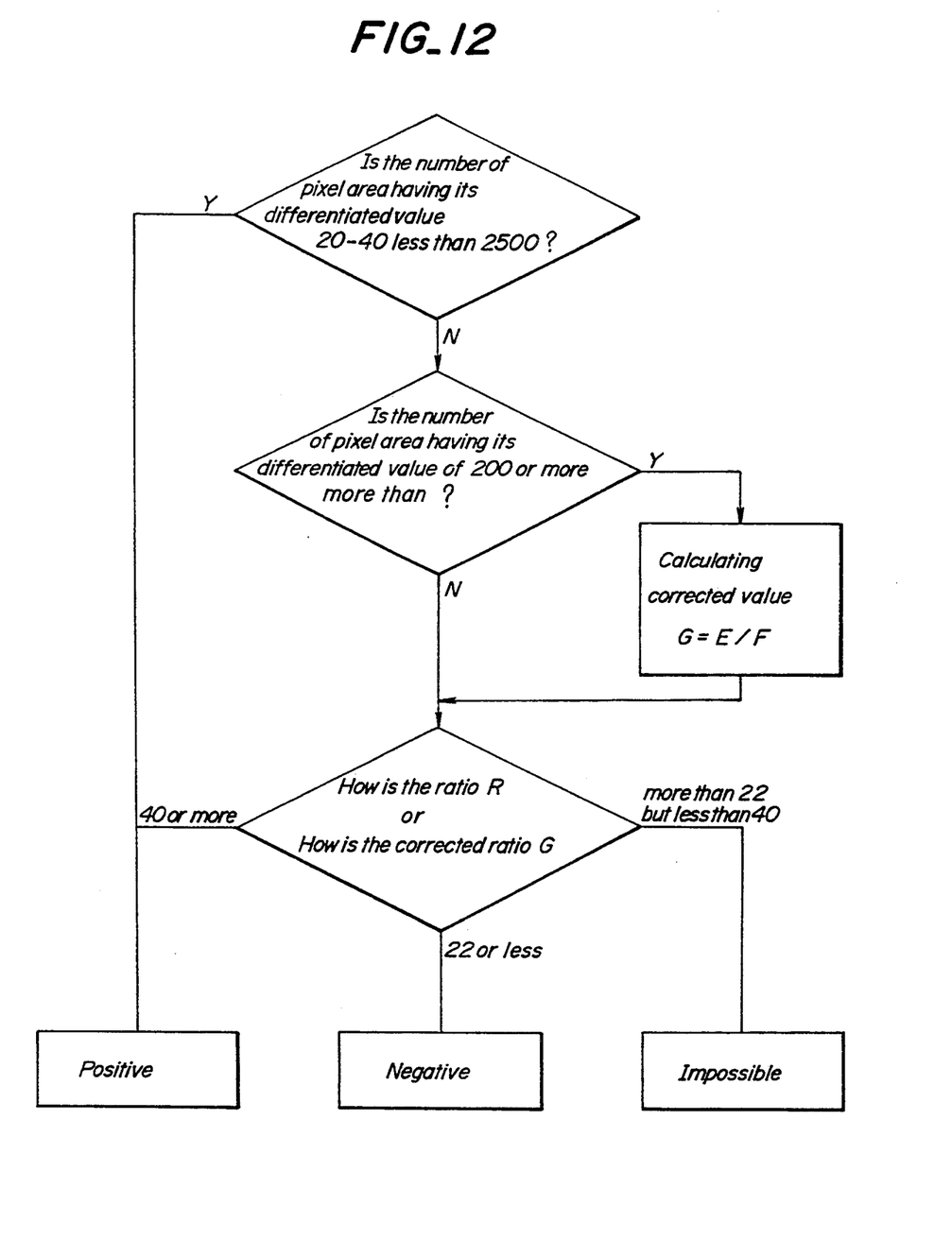
FIG. 12 is a flow chart showing a judging process executed in accordance with the third embodiment.

Successively calculating the pixel areas concerning all over the image information of the pattern in accordance with the above mentioned formulae to obtain the differentiating values of the pixel areas which cover all over the image of the well 11a. The thus obtained differentiated values of the two-dimensional image of the particle pattern are supplied to a judging circuit 48 and stored in a memory arranged in the circuit 48 successively. In the third embodiment, in the judging circuit 48, the particle pattern formed in the well 11a is judged from a distribution of the thus obtained differentiated values of the two-dimensional image of the particle pattern. One example of the judgement will be explained in the following, taking the flow chart shown in FIG. 12 as a reference. It should be noted that this example is for obtaining differentiated values concerning the particle pattern formed in the bottom surface of one well and for judging whether the particle pattern is agglutinated or not from a distribution of the thus obtained differentiated values of the pattern.

(1) Destruction of the particle pattern

When there are found more than two thousand and five hundred pixel areas having their differentiated values more than 20 but less than 40, it is judged that the particle pattern gets out shape. That is to say, when the particle pattern gets out shape, a large number of intermediate variations in the concentration of the particles appear in the particle pattern. Thus, when taking an attention into the fact, the number of the pixel areas having differentiated values between 20 and 40 are counted and the number exceeds over 2500, it can be judged the particle pattern gets out its shape. Since such destruction of the pattern appears only in agglutinated particle patterns, when such destruction is recognized in the particle pattern, the pattern is judged an agglutinated one.

(2) Bubbles

When there are found ten or more pixel areas having their differentiated value more than 200, it is judged as the particle pattern includes bubbles. That is to say, when the bubbles are included in the particle pattern, the difference between light and shade of the pattern becomes very large, so that many large differentiated values are be found. Therefore, the existence of bubbles in the particle pattern is judged by the number of the pixels having a large differentiated value.

(3) Agglutinated particle pattern (positive)

When a ratio, which is obtained by dividing a number of pixel areas A whose differentiated values are more than 20 but less than 50 by a number of pixel areas B whose differentiated values are more than 100 but less than 200, is more than 40, it is judged that the particle pattern is agglutinated.

(4) Non-agglutinated particle pattern (negative)

When the ratio mentioned in the above is less than 22, it is judged that the particle pattern is non-agglutinated.

(5) Impossible to be judged

A sample having the ratio more than 22 but less than 40 is judged as impossible to be judged. Such samples should be observed by the operator in a visual manner or re-examined.

When the particle pattern is judged as the pattern includes the bubbles, a ratio G, which is obtained by $G = E/F$ is compared with the above-mentioned ratio R; wherein the value E is obtained by multiplying the number of pixel areas having their differentiated values more than 20 but less than 50 by 1.2 and the value F is obtained by multiplying the number of pixels having their differentiated values more than 100 but less than 200 by 0.5. By multiplying the number of pixel areas having their differentiated values more than 20 but less than 50 by 1.2 and multiplying the number of pixel areas having their differentiated values more than 100 but less than 200 by 0.5, the small variation of the light and shade of the pattern is emphasized, and the large variation thereof is decreased, so that it is possible to judge the particle pattern without being influenced by the bubbles included in the particle pattern.

The thus obtained judgement result is supplied to an output device 49 to display it on a monitor screen thereof.

Distributions of the differentiated values of image signals, which are obtained by picking up two-dimensional images of particle patterns concerning various kinds of samples are shown in the following Table.

TABLE 1

| Differentiated value | Sample 1 | Sample 2 | Sample 3 | Sample 4 | Sample 5 | Sample 6 | Sample 7 | Sample 8 | Sample 9 |
|---|---|---|---|---|---|---|---|---|---|
| ~20 | 8314 | 8743 | 11875 | 9300 | 11449 | 8295 | 8314 | 8469 | 8427 |
| 20~30 | 3543 | 3803 | 827 | 3019 | 1336 | 3467 | 3449 | 3538 | 3545 |
| 30~40 | 1248 | 1364 | 248 | 951 | 480 | 1212 | 1239 | 1265 | 1323 |
| 40~50 | 380 | 304 | 174 | 313 | 243 | 312 | 323 | 283 | 255 |
| 50~60 | 139 | 45 | 135 | 142 | 198 | 242 | 277 | 226 | 242 |
| 60~70 | 84 | 4 | 125 | 96 | 118 | 168 | 133 | 92 | 104 |
| 70~80 | 65 | 1 | 134 | 79 | 79 | 83 | 80 | 53 | 49 |
| 80~90 | 67 | 0 | 123 | 55 | 84 | 75 | 64 | 51 | 38 |
| 90~100 | 58 | 0 | 124 | 44 | 71 | 70 | 58 | 43 | 48 |
| 100~110 | 72 | 0 | 106 | 34 | 52 | 57 | 40 | 40 | 45 |
| 110~120 | 49 | 0 | 84 | 32 | 43 | 66 | 52 | 52 | 45 |
| 120~130 | 61 | 0 | 58 | 18 | 24 | 41 | 46 | 46 | 46 |
| 130~140 | 64 | 0 | 35 | 28 | 7 | 38 | 43 | 32 | 33 |
| 140~150 | 50 | 0 | 28 | 21 | 2 | 39 | 45 | 23 | 15 |
| 150~160 | 35 | 0 | 28 | 13 | 5 | 40 | 28 | 15 | 16 |
| 160~170 | 26 | 0 | 28 | 21 | 3 | 31 | 14 | 11 | 12 |
| 170~180 | 7 | 0 | 14 | 15 | 0 | 19 | 8 | 9 | 9 |
| 180~190 | 9 | 0 | 8 | 16 | 2 | 9 | 7 | 4 | 2 |
| 190~200 | 6 | 0 | 10 | 13 | 0 | 5 | 6 | 2 | 0 |
| 200~210 | 1 | 0 | 5 | 14 | 0 | 3 | 1 | 1 | 0 |
| 210~220 | 1 | 0 | 2 | 9 | 0 | 2 | 0 | 0 | 0 |
| 220~230 | 0 | 0 | 9 | 5 | 0 | 0 | 0 | 0 | 0 |
| 230~240 | 0 | 0 | 0 | 1 | 0 | 0 | 0 | 0 | 0 |
| 240~255 | 0 | 0 | 3 | 19 | 0 | 0 | 0 | 0 | 0 |
| 200~ | 2 | 0 | 19 | 48 | 0 | 5 | 1 | 1 | 0 |
| 100~200 | 379 | 0 | 399 | 211 | 138 | 345 | 289 | 234 | 223 |
| 20~40 | 4791 | 5167 | 1075 | 3970 | 1816 | 4679 | 4688 | 4803 | 4868 |
| 20~50 | 5171 | 5471 | 1249 | 4283 | 2059 | 4991 | 5011 | 5086 | 5123 |
| 20~50/100~200(R) | 13.643799 | error | 3.1303258 | 20.298578 | 14.920289 | 14.466666 | 17.339100 | 21.735042 | 22.973094 |
| 0~255 | 14279 | 14264 | 14183 | 14258 | 14196 | 14274 | 14227 | 14258 | 14254 |
| E | | | 1498.8 | 5139.6 | | | | | |
| F | | | 199.5 | 105.5 | | | | | |
| Corrrected value G = E/F | | | 7.5127819 | 48.716587 | | | | | |
| Judgement | negative | positive | negative (bubble) | positive (bubble) | destruction | negative | negative | negative | impossible |

| Differentiated value | Sample 10 | Sample 11 | Sample 12 | Sample 13 | Sample 14 | Sample 15 | Sample 16 | Sample 17 | Sample 18 |
|---|---|---|---|---|---|---|---|---|---|
| ~20 | 8347 | 8431 | 8433 | 8390 | 8281 | 8223 | 8371 | 8268 | 8293 |

TABLE 1-continued

| | | | | | | | | | |
|---|---|---|---|---|---|---|---|---|---|
| 20~30 | 3618 | 3610 | 3649 | 3667 | 3654 | 3697 | 3707 | 3875 | 3810 |
| 30~40 | 1328 | 1330 | 1352 | 1355 | 1314 | 1365 | 1347 | 1346 | 1359 |
| 40~50 | 348 | 266 | 272 | 247 | 344 | 355 | 366 | 392 | 483 |
| 50~60 | 189 | 193 | 178 | 193 | 229 | 255 | 209 | 227 | 235 |
| 60~70 | 90 | 111 | 84 | 97 | 124 | 138 | 167 | 96 | 72 |
| 70~80 | 43 | 53 | 46 | 59 | 88 | 79 | 69 | 25 | 14 |
| 80~90 | 44 | 46 | 45 | 67 | 64 | 47 | 17 | 3 | 0 |
| 90~100 | 43 | 43 | 31 | 53 | 66 | 46 | 14 | 3 | 0 |
| 100~110 | 29 | 36 | 37 | 36 | 36 | 27 | 5 | 0 | 0 |
| 110~120 | 47 | 40 | 46 | 34 | 23 | 13 | 1 | 0 | 0 |
| 120~130 | 41 | 32 | 23 | 27 | 10 | 6 | 0 | 0 | 0 |
| 130~140 | 39 | 20 | 18 | 15 | 2 | 1 | 0 | 0 | 0 |
| 140~150 | 21 | 23 | 10 | 7 | 3 | 2 | 0 | 0 | 0 |
| 150~160 | 8 | 13 | 7 | 4 | 2 | 0 | 0 | 0 | 0 |
| 160~170 | 12 | 16 | 2 | 3 | 1 | 0 | 0 | 0 | 0 |
| 170~180 | 6 | 7 | 12 | 1 | 0 | 0 | 0 | 0 | 0 |
| 180~190 | 5 | 1 | 1 | 0 | 0 | 0 | 0 | 0 | 0 |
| 190~200 | 1 | 0 | 1 | 0 | 0 | 0 | 0 | 0 | 0 |
| 200~210 | 0 | 0 | 0 | 0 | 0 | 0 | 0 | 0 | 0 |
| 210~220 | 0 | 0 | 0 | 0 | 0 | 0 | 0 | 0 | 0 |
| 220~230 | 0 | 0 | 0 | 0 | 0 | 0 | 0 | 0 | 0 |
| 230~240 | 0 | 0 | 0 | 0 | 0 | 0 | 0 | 0 | 0 |
| 240~255 | 0 | 0 | 0 | 0 | 0 | 0 | 0 | 0 | 0 |
| 200~ | 0 | 0 | 0 | 0 | 0 | 0 | 0 | 0 | 0 |
| 100~200 | 209 | 188 | 147 | 127 | 77 | 49 | 6 | 0 | 0 |
| 20~40 | 4946 | 4940 | 5001 | 5022 | 4968 | 5062 | 5054 | 5221 | 5169 |
| 20~50 | 5294 | 5206 | 5273 | 5269 | 5312 | 5417 | 5420 | 5613 | 5652 |
| 20~50/100~200(R) | 25.330143 | 27.691489 | 35.870748 | 41.488188 | 68.987012 | 110.55102 | 903.33333 | error | error |
| 0~255 | 14259 | 14271 | 14237 | 14255 | 14241 | 14254 | 14273 | 14235 | 14266 |
| E | | | | | | | | | |
| F | | | | | | | | | |
| Corrected value G = E/F | | | | | | | | | |
| judgement | impossible | impossible | impossible | positive | positive | positive | positive | positive | positive |

In this table, there are indicated not only the number of pixel areas belonging to each differentiated value used in the above mentioned judgements, but also the numbers of pixel areas having their differentiated values more than 200, more than 100 but less than 200, more than 20 but less than 40, more than 20 but less than 50, the ratio R, less than 225, values of E and F, the corrected ratio G and the judgement result. The samples 1, 6, 7 and 8 are typical negative patterns, the samples 13 to 18 are typical positive patterns, and the samples 9 to 12 are impossible to be judged. Further, the samples 3 and 4 are judged as bubbles are included; and sample 3 is judged as negative and the sample 4 is judged as positive by using the corrected ratio G. The sample 5 is judged as the pattern gets out shape but finally judged as positive. As clear from the table and the above explanation, according to the third embodiment of the method of the invention, even in case bubbles are included in the sample or the particle pattern is destroyed, it is possible to judge whether the particle pattern is agglutinated or not in an exact manner. Therefore, the number of samples, which need to be tested in a visual manner or to be re-examined, becomes so small that the processing ability of an automatic judging apparatus can be increased. Particularly, in case the bubbles are included in the particle pattern, the pattern can be judged by using the corrected differentiated values. Therefore, the number of samples, which are judged as impossible to be tested, is decreased.

What is claimed is:

1. Particle pattern judging method comprising the steps of:

picking up a two dimensional image of a particle pattern formed on the bottom surface of a reaction vessel by an immunological agglutinating reaction to obtain an image information of the particle pattern;

differentiating said image information along a diameter passing through a center of the bottom surface of the reaction vessel to obtain differentiated values along said diameter; and judging whether the particle pattern is agglutinated or not by comparing said differentiated values along the diameter with a standard distribution of differentiated values which is previously obtained by using known agglutinated and non-agglutinated particle patterns;

wherein said differentiating step is conducted by using a first differentiation operator for detecting a variation of light intensity of the particle pattern in a horizontal direction and a second differentiation operator for detecting a variation of light intensity of the particle pattern in a vertical direction, said differentiating step comprising the steps of extracting a number of pixels, consisting of a pixel area from the image information of the particle pattern, and multiplying the light intensity of each pixel consisting of the pixel area by each coefficient of said first and second differentiation operators to obtain Y1 and Y2, Y1 being the value calculated by using the first differentiation operator and Y2 being the value calculated by using the second differentiation operator, obtaining a mean value of Y1 and Y2 by calculating the formula of $Y=(|Y1|+|Y2|)/2$ to get the differentiated value of the pixel area; and extract the pixel areas concerning all over the particle pattern in a successive manner.

2. Particle pattern judging method comprising the steps of:

picking up a two dimensional image of a particle pattern formed on the bottom surface of a reaction vessel by an immunological agglutinating reaction to obtain an image information of the particle pattern;

differentiating said image information along a diameter passing through a center of the bottom surface of the reaction vessel to obtain differentiated values along said diameter; and judging whether the particle pattern is agglutinated or not by comparing said differentiated values along the diameter with a standard distribution of differentiated values which is previously obtained by using known agglutinated and non-agglutinated particle patterns;

wherein said differentiating step is conducted by using a first differentiation operator for detecting a variation of light intensity of the particle pattern in a horizontal direction and a second differentiation operator for detecting a variation of light intensity of the particle pattern in a vertical direction, said differentiating step comprising the steps of extracting a number of pixels, consisting of a pixel area from the image information of the particle pattern and multiplying the light intensity of each pixel consisting of the pixel area by each coefficient of said first and second differentiation operators to obtain Y1 and Y2, Y1 being the value calculated by using the first differentiation operator and Y2 being the value calculated by using the second differentiation operator, obtaining a mean value of Y1 and Y2 by calculating the formula of $Y=(|Y1|+|Y2|)/2$ to get the differentiated value of the pixel area; and extract the pixel areas concerning all over the particle pattern in a successive manner, wherein Y1 and Y2 are calculated as follows:

$$Y1=(-1\times A)+(0\times B)+(1\times C)\\+(-2\times D)+(0\times E)+(2\times F)\\+(-1\times G)+(0\times H)+(-1\times I)$$

$$Y2=(-1\times A)+(-2\times B)+(-1\times C)\\+(0\times D)+(0\times E)+(0\times F)\\+(1\times G)+(2\times H)+(1\times I)$$

3. Particle pattern judging method according to claim 2, wherein:
said judging step comprises the step of judging as the particle pattern is agglutinated when there are found 2500 or more extracted pixels each having its differentiated value of more than 20 but less than 40.

4. Particle pattern judging method according to claim 2, wherein:
said judging step comprises the step of obtaining a first number of pixel areas each having its differentiated value of more than 20 but less than 50 and a second number of pixel areas each having its differentiated value of more than 100 but less than 200; judging as the particle pattern is agglutinated when the value, which is obtained by dividing the first pixel number by said second pixel number, is less than 22.

5. Particle pattern judging method according to claim 2, wherein:
said judging step is the step of obtaining a first pixel number of pixel areas each having its differentiated value of more than 20 but less than 50 and a second number of pixel areas each having its differentiated value of more than 100 but less than 200; judging as the particle pattern is non-agglutinated when the value, which is obtained by dividing the first pixel number by said second pixel number, is more than 40.

6. Particle pattern judging method according to claim 2, wherein:
said judging step comprises the step of obtaining a first number of pixel areas having its differentiated value of more than 20 but less than 50 and a second number of pixel areas having its differentiated value of more than 100 but less than 200; judging that it is impossible to judge the particle pattern when the value, which is obtained by dividing the first pixel number by said second pixel number, is more than 22 but less than 40.

* * * * *